(12) United States Patent
Yamada et al.

(10) Patent No.: US 10,082,525 B2
(45) Date of Patent: Sep. 25, 2018

(54) PROBE UNIT (71) Applicant: NHK Spring Co., Ltd., Yokohama-shi (JP)

(72) Inventors: Yoshio Yamada, Nagano (JP); Kohei Hironaka, Nagano (JP)

(73) Assignee: NHK Spring Co., Ltd., Yokohama-shi (JP)

( * ) Notice: Subject to any disclaimer, the term of this patent is extended or adjusted under 35 U.S.C. 154(b) by 8 days.

(21) Appl. No.: 15/511,733

(22) PCT Filed: Sep. 18, 2015

(86) PCT No.: PCT/JP2015/076789
§ 371 (c)(1),
(2) Date: Mar. 16, 2017

(87) PCT Pub. No.: WO2016/043327
PCT Pub. Date: Mar. 24, 2016

(65) Prior Publication Data
US 2017/0299631 A1    Oct. 19, 2017

(30) Foreign Application Priority Data

Sep. 19, 2014  (JP) ................................. 2014-191972

(51) Int. Cl.
*G01R 1/067*     (2006.01)
*G01R 1/073*     (2006.01)
*H01L 21/00*     (2006.01)

(52) U.S. Cl.
CPC ..... *G01R 1/07357* (2013.01); *G01R 1/06722* (2013.01); *G01R 1/07378* (2013.01);
(Continued)

(58) Field of Classification Search
CPC ....... H01L 21/00; H01L 2221/00; G01N 1/00; G01N 2201/00; G01R 1/00
See application file for complete search history.

(56) References Cited

U.S. PATENT DOCUMENTS

| 5,945,836 A * | 8/1999 | Sayre ................. G01R 1/07328 |
|---|---|---|
|  |  | 324/750.25 |
| 2003/0132773 A1 | 7/2003 | Brkovic et al. |

(Continued)

FOREIGN PATENT DOCUMENTS

| JP | 09-312185 A | 12/1997 |
|---|---|---|
| JP | 3090255 U | 11/2002 |

(Continued)

OTHER PUBLICATIONS

International Search Report dated Nov. 24, 2015, issued for PCT/JP2015/076789.

*Primary Examiner* — Jermele M Hollington
*Assistant Examiner* — Temilade Rhodes-Vivour
(74) *Attorney, Agent, or Firm* — Locke Lord LLP (57) ABSTRACT

A probe unit according to the present invention is suitable for allowing a large current to flow. In the probe unit that accommodates a plurality of contact probes for electrically connecting an inspection target object and a signal processing device used to output an inspection signal, both ends of a large current probe (3) are electrically connected to electrodes of a contact target object, and a large current is made to flow via a metal block (50) that comes into contact with both end portions of the large current probe (3).

9 Claims, 6 Drawing Sheets

(52) U.S. Cl.
CPC .......... *G01N 2201/00* (2013.01); *H01L 21/00* (2013.01); *H01L 2221/00* (2013.01)

(56) References Cited

U.S. PATENT DOCUMENTS

| | | | |
|---|---|---|---|
| 2009/0146672 A1* | 6/2009 | Nakamura | G01R 1/06722 324/754.03 |
| 2013/0099814 A1 | 4/2013 | Kazama et al. | |
| 2013/0141127 A1 | 6/2013 | Yasuta et al. | |
| 2014/0253163 A1* | 9/2014 | Suzuki | G01R 1/06722 324/755.05 |

FOREIGN PATENT DOCUMENTS

| | | |
|---|---|---|
| JP | 2010-267502 A | 11/2010 |
| JP | 2013-117476 A | 6/2013 |
| JP | 2013-224891 A | 10/2013 |
| WO | 2011/013731 A1 | 2/2011 |
| WO | 2011/162362 A1 | 12/2011 |

\* cited by examiner

PROBE UNIT

FIELD

The present invention relates to a probe unit used for inspecting a conduction state or operational characteristics of an inspection target object such as a semiconductor integrated circuit.

BACKGROUND

Conventionally, to inspect a conduction state or operational characteristics of an inspection target object such as a semiconductor integrated circuit and a liquid crystal panel, a probe unit that accommodates a plurality of contact probes is used for electrically connecting the inspection target object and a signal processing device that outputs an inspection signal. In recent years, with the high integration and the size reduction of semiconductor integrated circuits and liquid crystal panels, a technology applicable to the inspection target object that is highly integrated and reduced in size, by reducing the pitch between the contact probes in probe units has been advanced.

In addition, as the probe unit described above, a probe unit including a contact probe that electrically connects a semiconductor integrated circuit and a circuit board, by bringing both end portions of the contact probe into contact with an electrode of the semiconductor integrated circuit and an electrode of the circuit board that outputs an inspection signal has been disclosed (for example, see Patent Literature 1 and Patent Literature 2).

The contact probe disclosed in Patent Literature 1 includes a first conductive member that comes into contact with an electrode of a semiconductor integrated circuit; a second conductive member that comes into contact with an electrode of a circuit board that outputs an inspection signal; and a conductive coil spring that couples and energizes the first conductive member and the second conductive member. The contact probe disclosed in Patent Literature 2 is cooled from the inside using a tubular-shaped conductive member that is penetrated in the longitudinal direction, thereby preventing the resistance value from increasing.

In addition, a probe unit including a contact probe having a contact unit that comes into contact with an electrode of a semiconductor integrated circuit; and an elastic unit that is coupled to a conducting wire connected to a circuit board for outputting an inspection signal and the like. The elastic unit comes into contact with an end portion at a side different from a side that comes into contact with the semiconductor integrated circuit of the contact unit, has been disclosed (for example, see Patent Literature 3).

Furthermore, a probe unit including a contact probe that comes into contact with an electrode of a semiconductor integrated circuit, and that includes an elastically deformable elastic conductive plate as well as a guide tube that guides an expanding and contracting direction of the elastic conductive plate, has been disclosed (for example, see Patent Literature 4).

CITATION LIST

Patent Literature

Patent Literature 1: WO2011/013731
Patent Literature 2: Japanese Patent Application Laid-open No. 2010-267502
Patent Literature 3: Utility Model Registration No. 3090255
Patent Literature 4: Japanese Patent Application Laid-open No. 9-312185

SUMMARY

Technical Problem

In recent years, a contact probe capable of allowing a large current having a current value of about 1000 A or more to flow is demanded to inspect a semiconductor in a vehicle control system or the like. However, the conventional contact probe disclosed in Patent Literature 1 including a coil spring in the conduction path is not suitable for allowing a large current to flow because conduction often takes place at contact points such as a contact point between the first conductive member and the coil spring, and a contact point between the second conductive member and the coil spring, as well as a contact point between the first conductive member and the second conductive member; and the like.

In addition, the conventional contact probes disclosed in Patent Literature 2 to Patent Literature 4 are not suitable for allowing a large current to flow because a plate-shaped or wire-shaped member is conducted, which results in a small sectional area in the conduction path.

The present invention has been made in view of the above, and an object of the present invention is to provide a probe unit suitable for allowing a large current to flow.

Solution to Problem

To solve the above-described problem and achieve the object, a probe unit according to the present invention includes: first and second contact probes that come into contact with respective electrodes of a contact target object being different from each other at one end portion side in a longitudinal direction, and that come into contact with respective electrodes of a substrate being different from each other at another end portion side; and a probe holder that accommodates and holds the first and the second contact probes, wherein the first contact probe is formed of a conductive material and is expandable and contractible in the longitudinal direction, the second contact probe includes a first contact unit that is formed of a conductive material and that comes into contact with an electrode of the contact target object, a second contact unit that is formed of a conductive material and that comes into contact with an electrode of the substrate, and a coupling member that is expandable and contractible in the longitudinal direction and that couples the first and the second contact units, the probe holder includes a conductive block that is formed of a conductive material and that is formed with a plurality of first insertion holes to which the first and the second contact probes are inserted, and an insulating block that is provided inside the conductive block, that is formed of a material having an insulating property, and that is formed with a plurality of second insertion holes to which the first and the second contact probes are inserted, the first and the second contact units each come into contact with the conductive block, and the insulating block at least prevents the first contact probe from loosening.

Moreover, in the above-described probe unit according to the present invention, the coupling member is formed of a material at least a surface of which has an insulating property.

Moreover, in the above-described probe unit according to the present invention further includes: a conductive member that is held by the probe holder, the conductive member being electrically connected to the second contact probe, and being formed of a conductive material.

Moreover, in the above-described probe unit according to the present invention, the conductive member is a conductive pin having a substantially columnar shape, and is pressed into one of the first insertion holes.

Moreover, in the above-described probe unit according to the present invention, a first insertion hole, among the first insertion holes, into which the conductive member is inserted has a stepped shape having a diameter that increases toward outside, the conductive member includes a conductive nut provided on the insulating block, and two conductive screws screwed into the nut from an upper surface and a lower surface of the conductive block, and a head portion of each of the screws abuts on a step part formed on the first insertion hole.

Moreover, in the above-described probe unit according to the present invention, the probe holder and the substrate are separated, while the first and the second contact probes and the electrodes of the substrate are brought into contact with each other.

Moreover, the above-described probe unit according to the present invention further includes an air supplying mechanism configured to send gas to flow through space between the probe holder and the substrate.

Moreover, in the above-described probe unit according to the present invention, a plurality of nail portions each including a tapered tip end are provided on a tip end of at least one of the first and the second contact units, at a side that comes into contact with the electrode.

Moreover, in the above-described probe unit according to the present invention, the probe holder further includes: a first insulating plate formed of an insulating material and provided on one surface of the conductive block, the first insulating plate including first holes to which a part of the first contact probe is inserted, and second holes to which a part of the second contact probe is inserted, wherein the first and the second holes are positioned in correspondence with an electrode arrangement of the contact target object; and a second insulating plate formed of an insulating material and provided on another surface of the conductive block, the second insulating plate including third holes to which a part of the first contact probe is inserted, and fourth holes to which a part of the second contact probe is inserted, wherein the third and the fourth holes are positioned in a same arrangement as the first and the second holes.

Advantageous Effects of Invention

The present invention exhibits advantageous effects in allowing a large current to flow because both ends of a first contact probe are electrically connected to electrodes of a connection target object, and a large current is made to flow via a conductive block that comes into contact with both end portions of the first contact probe, or the conductive block and a conductive member that comes into contact with the conductive block.

DESCRIPTION OF EMBODIMENTS

Hereinafter, best modes for carrying out the present invention will be described in detail with reference to the accompanying drawings. It is noted that the present invention is not limited to the following embodiments. In addition, the drawings referred to in the following descriptions merely schematically illustrate the shape, the size, and the positional relation to the extent that the contents of the present invention can be understood. In other words, the shape, the size, and the positional relation of the present invention are not limited only to those illustrated in the drawings.

First Embodiment

Figure 1:
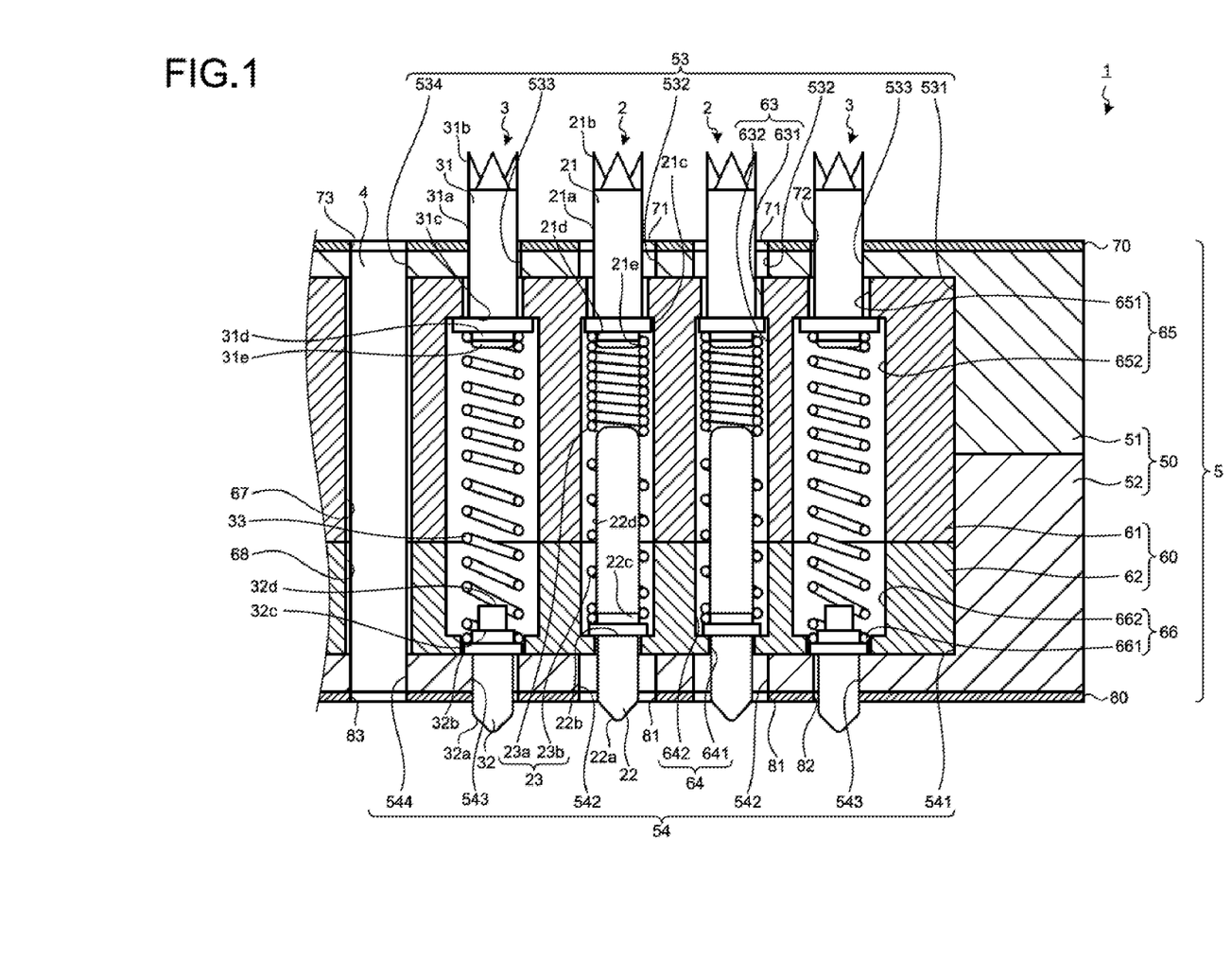
FIG. 1 is a partial sectional view illustrating a configuration of a probe unit according to a first embodiment of the present invention.

FIG. 1 is a partial sectional view illustrating a configuration of a probe unit according to a first embodiment of the present invention. A probe unit 1 illustrated in FIG. 1 is a device used for inspecting the electrical characteristics of a semiconductor integrated circuit that is an inspection target object, and for supplying power to the semiconductor integrated circuit. The probe unit 1 is also a device that electrically connects between an electrode of the semiconductor integrated circuit and an electrode of a circuit board that outputs an inspection signal to the semiconductor integrated circuit.

The probe unit 1 includes: contact probes 2 for a signal (hereinafter, simply referred to as "signal probes 2") that comes into contact with each electrode of a semiconductor integrated circuit that is a contact target body contacted at one end portion side in a longitudinal direction, and that transmits an inspection signal; and contact probes 3 for a large current (hereinafter, simply referred to as "large current probes 3") that comes into contact with each electrode of a circuit that causes a large current to flow in the semiconductor integrated circuit that is the contacted target body contacted at one end portion side in the longitudinal direction. The probe unit 1 also includes a conductive pin 4 having a substantially columnar shape that can be electrically connected to each of both end portions of the large current probes 3; and a plurality of probe holders 5 that accommodate and hold the signal probes 2, the large current probes 3, and the conductive pins 4 according to a predetermined pattern. The probe unit 1 may also include a holder member that is provided around the periphery of each of the probe holders 5, and that prevents a semiconductor package being in contact with the signal probes 2 from being displaced, during inspection.

The signal probe 2 is formed of a conductive material, and includes: a first plunger 21 that comes into contact with a connection electrode of the semiconductor integrated circuit when the semiconductor integrated circuit is to be inspected; a second plunger 22 that comes into contact with an electrode of the circuit board including an inspection circuit; and a coil spring 23 that is provided between the first plunger 21 and the second plunger 22 and that couples the first plunger 21 and the second plunger 22 in an expandable and contractible manner.

The first plunger 21 coaxially includes: a tip end portion 21a that has a plurality of nail portions 21b (apex portion) each having a tapered tip end; a flange unit 21c that extends from a base end side of the tip end portion 21a, and that has a diameter larger than that of the tip end portion 21a; a boss unit 21d that extends from an end portion different from the side that continues to the tip end portion 21a of the flange unit 21c, and that has a diameter smaller than that of the flange unit 21c; and a base end portion 21e that extends from an end portion different from the side that continues to the flange unit 21c of the boss unit 21d, and that has a diameter substantially the same as that of the boss unit 21d.

The second plunger 22 coaxially includes: a tip end portion 22a having a tapered tip end; a flange unit 22b that extends from the base end side of the tip end portion 22a, and that has a diameter larger than that of the tip end portion 22a; a boss unit 22c that extends from an end portion different from the side that continues to the tip end portion 22a of the flange unit 22b, and that has a diameter substantially the same as that of the boss unit 21d; and a base end portion 22d that extends from an end portion different from the side that continues to the flange unit 22b of the boss unit 22c, and that has a diameter equal to or slightly smaller than those of the boss units 21d and 22c. The tip end portion 22a has a substantially spindle shape with a single apex portion.

In the coil spring 23, the first plunger 21 side is a tightly wound portion 23a that is wound in an inner diameter substantially the same as the diameter of the boss unit 21d, and the second plunger 22 side is a roughly wound portion 23b that is wound at a predetermined pitch and in an inner diameter of equal to or more than the diameter of the base end portion 22d. For example, the end portion of the tightly wound portion 23a is pressed into the boss unit 21d, and abuts on the flange unit 21c. The end portion of the roughly wound portion 23b is pressed into the boss unit 22c, and abuts on the flange unit 22b. Using the coil spring 23 causes the base end portion 22d to be slid into the tightly wound portion 23a when a predetermined load is applied to the signal probe 2, thereby allowing the base end portion 22d and the tightly wound portion 23a to be electrically conducted.

Similar to the signal probe 2, the large current probe 3 is formed of a conductive material. The large current probe 3 includes: a first plunger 31 (first contact unit) that comes into contact with a connection electrode of the semiconductor integrated circuit, when the semiconductor integrated circuit is to be inspected; a second plunger 32 (second contact unit) that comes into contact with an electrode of the circuit board including an inspection circuit; and a coil spring 33 (coupling member) that is provided between the first plunger 31 and the second plunger 32, and that couples the first plunger 31 and the second plunger 32 in an expandable and contractible manner.

The first plunger 31 coaxially includes: a tip end portion 31a that has a plurality of nail portions 31b each having a tapered tip end; a flange unit 31c that extends from the base end side of the tip end portion 31a, and that has a diameter larger than that of the tip end portion 31a; a boss unit 31d that extends from an end portion different from the side that continues to the tip end portion 31a of the flange unit 31c, and that has a diameter smaller than that of the flange unit 31c; and a base end portion 31e that extends from an end portion different from the side that continues to the flange unit 31c of the boss unit 31d, and that has a diameter substantially the same as that of the boss unit 31d.

The second plunger 32 coaxially includes: a tip end portion 32a having a tapered tip end; a flange unit 32b that extends from the base end side of the tip end portion 32a, and that has a diameter larger than that of the tip end portion 32a; a boss unit 32c that extends from an end portion different from the side that continues to the tip end portion 32a of the flange unit 32b, and that has a diameter substantially the same as that of the boss unit 31d; and a base end portion 32d that extends from an end portion different from the side that continues to the flange unit 32b of the boss unit 32c, and that has a diameter substantially the same or slightly smaller than those of the boss units 31d and 32c.

The coil spring 33 is made of a wire material that is wound at a predetermined pitch and in an inner diameter substantially the same as those of the boss units 31d and 32c. For example, when the inner diameter is substantially the same as that of the boss unit 31d, one end portion of the coil spring 33 is pressed into the boss unit 31d, and abuts on the flange unit 31c. The other end portion of the coil spring 33 is pressed into the boss unit 32c, and abuts on the flange unit 32b.

In addition, the coil spring 33 is formed of a wire material at least the outer surface of which has an insulating property. For example, the wire material used for the coil spring 33 includes a resin material having an insulating property, and a wire material formed of a material the metal surface of which is coated with resin having an insulating property (such as Teflon (registered trademark)).

The conductive pin 4 is formed of a conductive metal material and is electrically connected to the large current probe 3 via a metal block 50, which will be described later. The conductive pin 4 may be formed of resin and the like, as long as the material has conductivity. In addition, the diameter of the conductive pin 4 in a direction orthogonal to the longitudinal direction is preferably equal to or more than the diameters of the tip end portions 31a and 32a.

The probe holder 5 includes: the metal block 50 (conductive block) that is formed of a conductive material such as metal and that is formed by laminating a first member 51 being placed on the upper surface side and a second member 52 being placed on the lower surface side in FIG. 1; an insulating block 60 that is formed of an insulating material such as resin, machinable ceramic, and silicon, and that is accommodated inside the metal block 50; a first insulating plate 70 that is formed of an insulating material such as resin, machinable ceramic, and silicon, that has a substantially plate shape, and that is disposed on the upper surface of the first member 51; and a second insulating plate 80 that is formed of an insulating material such as resin, machinable ceramic, and silicon, that has a substantially plate shape, and that is disposed on the lower surface of the second member 52.

Each of the metal block 50, the insulating block 60, the first insulating plate 70, and the second insulating plate 80 is fixed using an adhesive agent such as resin, or a screw.

The first member 51 and the second member 52 may be formed of a metal material including alloy such as brass and any material as long as the material has conductivity. From the viewpoint of strength as a probe holder, the first member 51 and the second member 52 are preferably formed of a metal material (including alloy).

Holder holes 53 and 54 for accommodating the signal probe 2, the large current probe 3, the conductive pin 4, and the insulating block 60 are respectively formed on the first member 51 and the second member 52. The holder hole 53 includes: an accommodation unit 531 that has an opening on the lower surface side (side facing the second member 52), and that accommodates a part of the insulating block 60; a hole 532 that communicates with the accommodation unit 531, that has an opening on the upper surface side, and into which a part of the signal probe 2 is inserted; a hole 533 that communicates with the accommodation unit 531, that has an opening on the upper surface side, and into which the large current probe 3 is slidably inserted; and a hole 534 that communicates with the accommodation unit 531 and into which the conductive pin 4 is inserted. The diameter of the hole 534 is the same or slightly smaller than the diameter of the conductive pin 4.

The holder hole 54 includes: an accommodation unit 541 that has an opening on the upper surface side (side facing the first member 51), and that accommodates a part of the insulating block 60; a hole 542 that communicates with the accommodation unit 541, that has an opening on the lower surface side, and into which the signal probe 2 is inserted; a hole 543 that communicates with the accommodation unit 541, that has an opening on the lower surface side, and into which the large current probe 3 is inserted; and a hole 544 that communicates with the accommodation unit 541 and into which the conductive pin 4 is inserted. The diameter of the hole 543 is slightly larger than the diameter of the tip end portion 32a. The diameter of the hole 544 is the same or slightly smaller than the diameter of the conductive pin 4.

When the first member 51 and the second member 52 are laminated, the holder holes 53 and 54 form hollow space having a substantially prism shape in which the inner wall surfaces of the accommodation unit 531 and the accommodation unit 541 are continuously linked. The hollow space has substantially the same shape as that of the outer periphery of the insulating block 60. The hollow space may be the same shape as that of the outer periphery of the insulating block 60, may be slightly larger for disposing an adhesive agent and the like, or may be slightly smaller so as to be pressed against the insulating block 60. The hole 532 and the hole 542 are formed coaxially. Similarly, the hole 533 and the hole 543 are formed coaxially, and the hole 534 and the hole 544 are formed coaxially.

The insulating block 60 is formed by laminating a first member 61 being placed on the upper surface side and a second member 62 being placed on the lower surface side in FIG. 1. The insulating block 60 has a substantially rectangular parallelepiped shape so that the insulating block 60 can be accommodated in the accommodation unit 531 and the accommodation unit 541.

The same number of holder holes 63 and 64 for accommodating the signal probe 2 are respectively formed on the first member 61 and the second member 62. The holder holes 63 and 64 that are insertion holes for accommodating the signal probe 2 are formed coaxially.

In addition, the same number of holder holes 65 and 66 for accommodating the large current probe 3 are respectively formed on the first member 61 and the second member 62, and the holder holes 65 and 66 that are insertion holes for accommodating the large current probe 3 are formed coaxially.

Furthermore, the same number of holder holes 67 and 68 for accommodating the conductive pin 4 are respectively formed on the first member 61 and the second member 62, and the holder holes 67 and 68 that are insertion holes for accommodating the conductive pin 4 are formed coaxially.

The holder holes 63 and 64 each have a stepped-hole shape having a diameter that varies along the penetrating direction. The holder hole 63 includes a small diameter unit 631 that has an opening on the upper surface side of the first member 61, and a large diameter unit 632 that communicates with the small diameter unit 631 and that has a diameter larger than that of the small diameter unit 631. The diameter of the small diameter unit 631 is slightly larger than that of the tip end portion 21a. The diameter of the large diameter unit 632 is slightly larger than the diameter of the flange unit 21c and/or the diameter of the coil spring 23.

The holder hole 64 includes a small diameter unit 641 that has an opening on the lower surface side of the second member 62, and a large diameter unit 642 that communicates with the small diameter unit 641 and that has a diameter larger than that of the small diameter unit 641. The diameter of the small diameter unit 641 is slightly larger than that of the tip end portion 22a. In addition, the diameter of the large diameter unit 642 is slightly larger than the diameter of the flange unit 22b and/or the diameter of the coil spring 23, and is substantially the same as that of the large diameter unit 632. The shapes of the holder holes 63 and 64 are determined according to the configuration of the signal probe 2 to be accommodated.

The holder holes 65 and 66 each have a stepped-hole shape having a diameter that varies along the penetrating direction. The holder hole 65 includes a small diameter unit 651 that has an opening on the upper surface side of the first member 61, and a large diameter unit 652 that communicates with the small diameter unit 651 and that has a diameter larger than that of the small diameter unit 651. The diameter of the small diameter unit 651 is slightly larger than that of the tip end portion 31a, and is larger than that of the hole 533. In addition, the diameter of the large diameter unit 652 is slightly larger than the diameter of the flange unit 31c and/or the diameter of the coil spring 33.

The holder hole 66 includes a small diameter unit 661 that has an opening on the lower surface side of the second member 62, and a large diameter unit 662 that communicates with the small diameter unit 661 and that has a diameter larger than that of the small diameter unit 661. The diameter of the small diameter unit 661 is slightly larger than the diameter of the flange unit 32b and/or the diameter of the coil spring 33. In addition, the diameter of the large diameter unit 662 is large than that of the small diameter unit 661, and is substantially the same as that of the large diameter unit 652. The shapes of the holder holes 65 and 66 are determined according to the configuration of the large current probe 3 to be accommodated.

Each of the holder holes 67 and 68 forms hollow space having a cylindrical shape with the same diameter. The diameters of the holder holes 67 and 68 are slightly larger than that of the conductive pin 4. The shapes of the holder holes 67 and 68 are determined according to the configuration of the conductive pin 4 to be accommodated.

In the first insulating plate 70, holes corresponding to the arrangement of the holes 532, 533, and 534 are formed on the upper surface of the first member 51. More specifically, the first insulating plate 70 is provided with a hole 71 (first hole) that is provided corresponding to the hole 532 and into which one or a plurality of the signal probes 2 is inserted; a hole 72 (second hole) that is provided corresponding to the hole 533 and into which the large current probe 3 is inserted;

and a hole 73 that is provided corresponding to the hole 534 and is capable of receiving the conductive pin 4.

In the second insulating plate 80, holes corresponding to the arrangement of the holes 542, 543, and 544 are formed on the lower surface of the second member 52. More specifically, the second insulating plate 80 is provided with a hole 81 (third hole) that is provided corresponding to the hole 542, and into which one or a plurality of the signal probes 2 is inserted; a hole 82 (fourth hole) that is provided corresponding to the hole 543, and into which the large current probe 3 is inserted; and a hole 83 that is provided corresponding to the hole 544, and is capable of receiving the conductive pin 4. In the second insulating plate 80, the holes 81, 82, and 83 are respectively formed in the same arrangement as that of the holes 71, 72, and 73.

In the probe holder 5, the hole 533, the hole 543, the holder hole 65, the holder hole 66, the hole 72, and the hole 82 are coaxial when the insulating block 60, the first insulating plate 70, and the second insulating plate 80 are fixed on the metal block 50. In addition, the hole 534, the hole 544, the holder hole 67, the holder hole 68, the hole 73, and the hole 83 are also formed coaxially.

In the signal probe 2, the tip end portion 21a of the first plunger 21 is protruded to the outside from the hole 71, and the tip end portion 22a of the second plunger 22 is protruded to the outside from the hole 81. The flange unit 21c has a function of preventing the signal probe 2 from coming loose from the probe holder 5, by abutting on the boundary wall surface between the small diameter unit 631 and the large diameter unit 632 of the holder hole 63. In addition, the flange unit 22b of the second plunger 22 has a function of preventing the signal probe 2 from coming loose from the probe holder 5, by abutting on the boundary wall surface between the small diameter unit 641 and the large diameter unit 642 of the holder hole 64.

In the large current probe 3, the tip end portion 31a of the first plunger 31 is protruded to the outside from the hole 72, and the tip end portion 32a of the second plunger 32 is protruded to the outside from the hole 82. The flange unit 31c has a function of preventing the large current probe 3 from coming loose from the probe holder 5, by abutting on the boundary wall surface between the small diameter unit 651 and the large diameter unit 652 of the holder hole 65. In addition, the flange unit 32b of the second plunger 32 has a function of preventing the large current probe 3 from coming loose from the probe holder 5, by abutting on the boundary wall surface between the hole 543 and the small diameter unit 661.

The metal block 50 holds the conductive pin 4, when both end portions of the conductive pin 4 are pressed into the holes 534 and 544, respectively.

Figure 2:
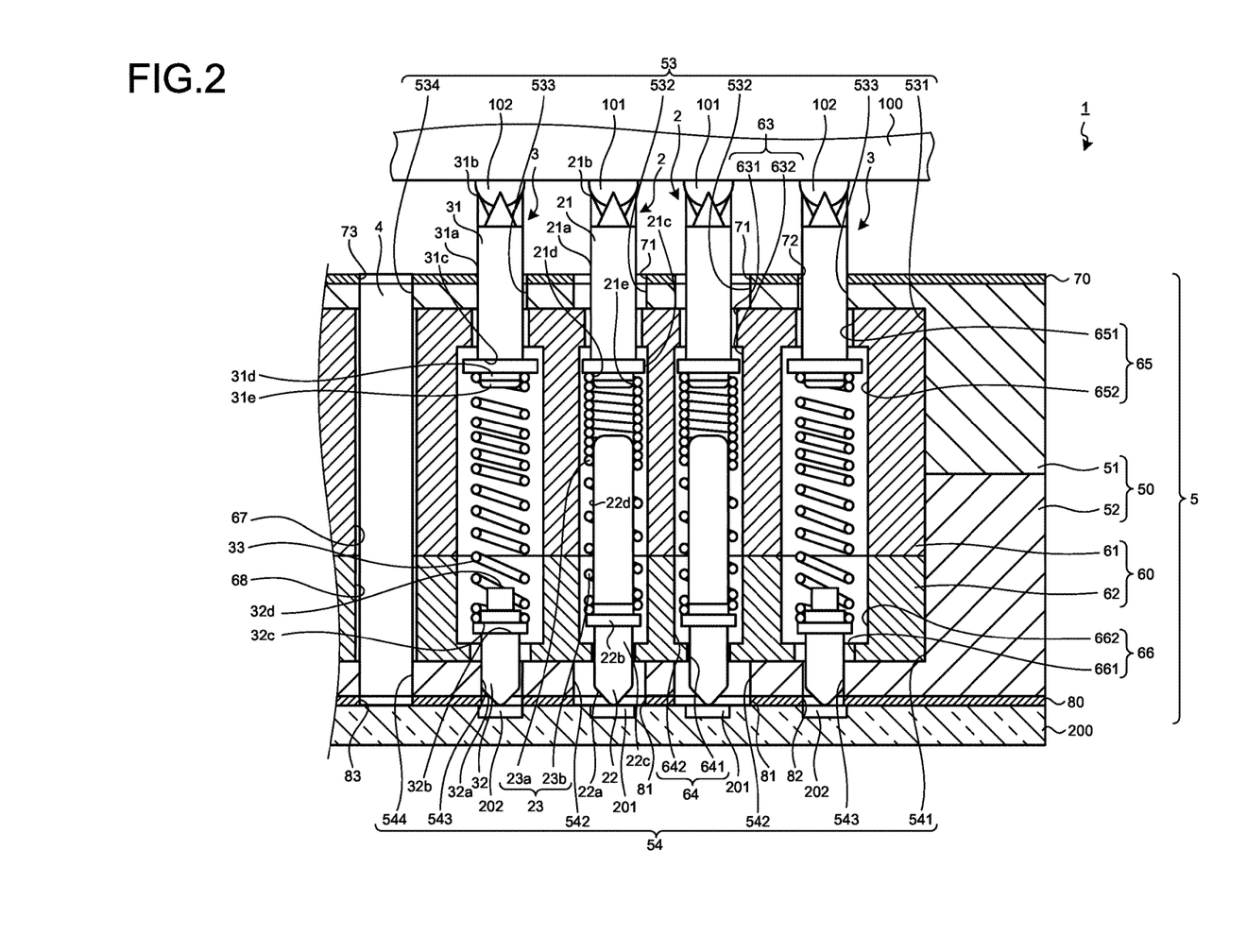
FIG. 2 is a partial sectional view illustrating a configuration of the probe unit according to the first embodiment of the present invention, when a semiconductor integrated circuit is to be inspected.

FIG. 2 is a partial sectional view illustrating a configuration of the probe unit according to the present embodiment, when a semiconductor integrated circuit is to be inspected, and is a diagram illustrating a state when a semiconductor integrated circuit 100 is inspected using the probe holder 5. As illustrated in FIG. 2, when the semiconductor integrated circuit 100 is to be inspected, one end of the signal probe 2 comes into contact with a signal connection electrode 101 of the semiconductor integrated circuit 100, and the other end of the signal probe 2 comes into contact with a signal connection electrode 201 of a circuit board 200. In addition, one end of the large current probe 3 comes into contact with a power supply connection electrode 102 of the semiconductor integrated circuit 100, and the other end of the large current probe 3 comes into contact with a power supply connection electrode 202 of the circuit board 200. In this process, the coil springs 23 and 33 are compressed along the longitudinal direction, by the contact load from the semiconductor integrated circuit 100.

In the signal probe 2, when the coil spring 23 is compressed by the contact load from the semiconductor integrated circuit 100, the base end portion 22d of the second plunger 22 enters the inside of the tightly wound portion 23a, and is brought into slidable contact with the inner peripheral side of the tightly wound portion 23a. In this process, the axis of the second plunger 22 does not deviate largely, which makes the slidable contact between the base end portion 22d and the inner periphery of the tightly wound portion 23a stable. Furthermore, the tightly wound portion 23a meanders slightly, which makes the contact resistance between the base end portion 22d and the coil spring 23 stable. In this manner, reliable conduction can be obtained.

The inspection signal supplied from the circuit board 200 to the semiconductor integrated circuit 100 during inspection arrives the signal connection electrode 101 of the semiconductor integrated circuit 100, from the signal connection electrode 201 of the circuit board 200, via the signal probe 2. More specifically, in the signal probe 2, the inspection signal arrives the signal connection electrode 101 of the semiconductor integrated circuit 100, via the second plunger 22, the tightly wound portion 23a, and the first plunger 21. In this manner, in the signal probe 2, the first plunger 21 and the second plunger 22 are conducted via the tightly wound portion 23a. Hence, it is possible to minimize the conduction path of the electric signal. Thus, it is possible to prevent a signal from flowing into the roughly wound portion 23b during inspection, and reduce and stabilize the inductance.

The power supply signal supplied to the semiconductor integrated circuit 100 from the circuit board 200 during inspection arrives the power supply connection electrode 102 of the semiconductor integrated circuit 100 from the power supply connection electrode 202 of the circuit board 200, via the large current probe 3. More specifically, the power supply signal arrives the power supply connection electrode 102 of the semiconductor integrated circuit 100 from the power supply connection electrode 202, via the second plunger 32 (tip end portion 32a) of the large current probe 3, the second member 52, the conductive pin 4, the first member 51, and the first plunger 31 (tip end portion 31a). In this manner, in the large current probe 3, a path for the power supply signal is formed by bringing the tip end portion 32a into contact with the inner wall surface of the hole 543, bringing the conductive pin 4 into contact with the inner wall surface of the hole 544, bringing the conductive pin 4 into contact with the inner wall surface of the hole 534, and bringing the tip end portion 31a into contact with the inner wall surface of the hole 533.

In addition, when the conductive pin 4 is not disposed, the power supply signal that is supplied from the circuit board 200 to the semiconductor integrated circuit 100 during inspection arrives the power supply connection electrode 102 of the semiconductor integrated circuit 100 from the power supply connection electrode 202 of the circuit board 200, via the large current probe 3 and the metal block 50. More specifically, the power supply signal arrives the power supply connection electrode 102 of the semiconductor integrated circuit 100 from the power supply connection electrode 202, via the second plunger 32 (tip end portion 32a) of the large current probe 3, the second member 52, the first member 51, and the first plunger 31 (tip end portion 31a). In this manner, in the large current probe 3, a path for the power supply signal is formed by bringing the tip end portion 32a into contact with the inner wall surface of the hole 543, bringing the first member 51 into laminating contact (electrical connection) with the second member 52, and bringing the tip end portion 31a into contact with the inner wall surface of the hole 533.

In addition, because the tip ends of the nail portions 21b and 31b are formed in a tapered shape, even if an oxide film is formed on the surface of the connection electrodes (signal connection electrode 101 and power supply connection electrode 102), it is possible to break through the oxide film, and bring the tip ends of the nail portions 21b and 31b directly into contact with the connection electrodes.

In the first embodiment described above, both ends of the large current probe 3 are electrically connected to the contact target electrodes, and a large current is made to flow via the metal block 50 that comes into contact with both end portions of the large current probe 3, or the metal block 50 and the conductive pin 4 that comes into contact with the metal block 50. Consequently, it is possible to obtain a probe unit suitable for allowing a large current to flow.

In this example, when a current is applied to the large current probe 3 without the metal block 50 and the like being interposed, a large amount of heat is generated to the large current probe 3, compared to when a current is applied to the large current probe 3 via the metal block 50, due to the internal resistance and the contact resistance with the electrode. Thus, there is a possibility that the conduction characteristics of the large current probe 3 may be degraded, due to the generated heat.

First Modification of First Embodiment

Figure 3:
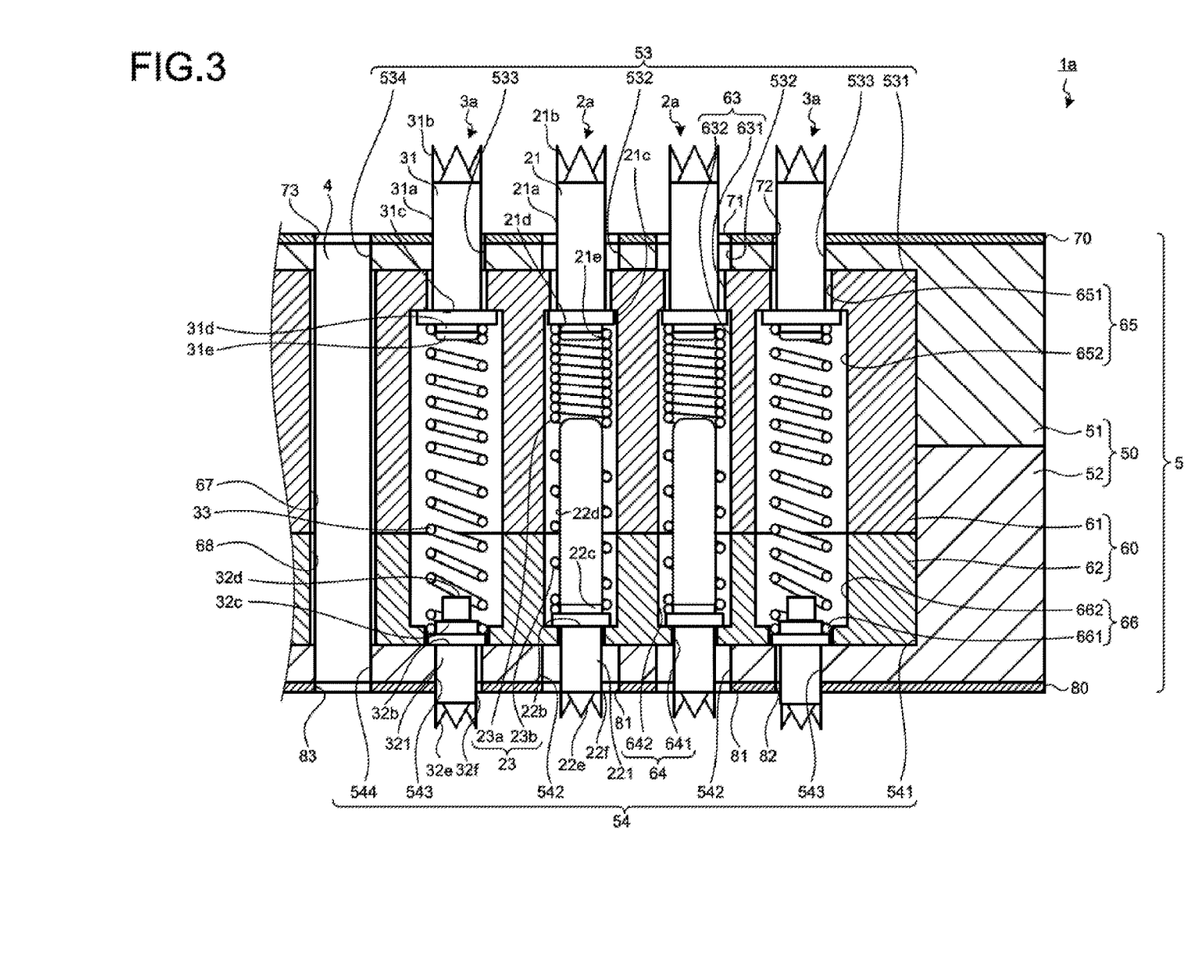
FIG. 3 is a partial sectional view illustrating a configuration of a probe unit according to a first modification of the first embodiment of the present invention.

FIG. 3 is a partial sectional view illustrating a configuration of a probe unit according to a first modification of the first embodiment. While in the first embodiment described above, the respective tip end portions 22a and 32a of the second plungers 22 and 32 have a substantially spindle shape with a single apex portion, the respective tip end portions 22a and 32a of the second plungers 22 and 32 have a plurality of apex portions as the tip end portions 21a and 31a described above, in a probe unit 1a according to the present first modification.

A signal probe 2a according to the first modification includes the first plunger 21 and the coil spring 23 described above, and a second plunger 221 (second contact member) that comes into contact with an electrode of the circuit board including an inspection circuit.

The second plunger 221 coaxially includes: a tip end portion 22f (second contact unit) that has a plurality of nail portions 22e (apex portions) each having a tapered tip end; the flange unit 22b that extends from the base end side of the tip end portion 22f, and that has a diameter equal to or larger than that of the tip end portion 22f; the boss unit 22c that extends from an end portion different from the side that continues to the tip end portion 22f of the flange unit 22b, and that has a diameter substantially the same as that of the boss unit 21d; and the base end portion 22d described above.

A large current probe 3a according to the first modification includes the first plunger 31 and the coil spring 33 described above, and a second plunger 321 (second contact member) that comes into contact with an electrode of the circuit board including an inspection circuit.

The second plunger 321 coaxially includes: a tip end portion 32f (second contact unit) that has a plurality of nail portions 32e (apex portions) each having a tapered tip end; the flange unit 32b that extends from the base end side of the tip end portion 32f, and that has a diameter larger than that of the tip end portion 32f; the boss unit 32c that extends from an end portion different from the side that continues to the tip end portion 32f of the flange unit 32b, and that has a diameter substantially the same as that of the boss unit 31d; and the base end portion 32d described above.

During the inspection, the tip end portions 22f and 32f come into contact with the signal connection electrode 201 and the power supply connection electrode 202 described above, respectively. In this process, the tip end portions 22f and 32f are brought into point-to-point contact with the contact surfaces of the signal connection electrode 201 and the power supply connection electrode 202, at a plurality of locations, by the nail portions 22e and 32e. Consequently, it is possible to reduce the contact resistance between the tip end portion 22f and the signal connection electrode 201, as well as the contact resistance between the tip end portion 32f and the power supply connection electrode 202.

In the first modification described above, the tip end portions 22f and 32f of the second plungers 221 and 321 are provided with the plurality of nail portions 22e and 32e (apex portions) each having a tapered tip end. Thus, it is possible to suppress the amount of heat generated by reducing the contact resistance between the tip end portions 22f and 32f and the signal connection electrode 201 and the power supply connection electrode 202, respectively, and to prevent the conduction characteristics of the large current probe 3 from being degraded.

In the first modification described above, the second plunger 321 in which a large current flows is provided with the plurality of nail portions 32e (apex portions) each having a tapered tip end. Thus, it is possible to suppress the amount of heat generated by the probe, and prevent the conduction characteristics from being degraded. Consequently, the tip end portion of the large current probe may at least include a plurality of the apex portions.

Second Modification of First Embodiment

Figure 4:
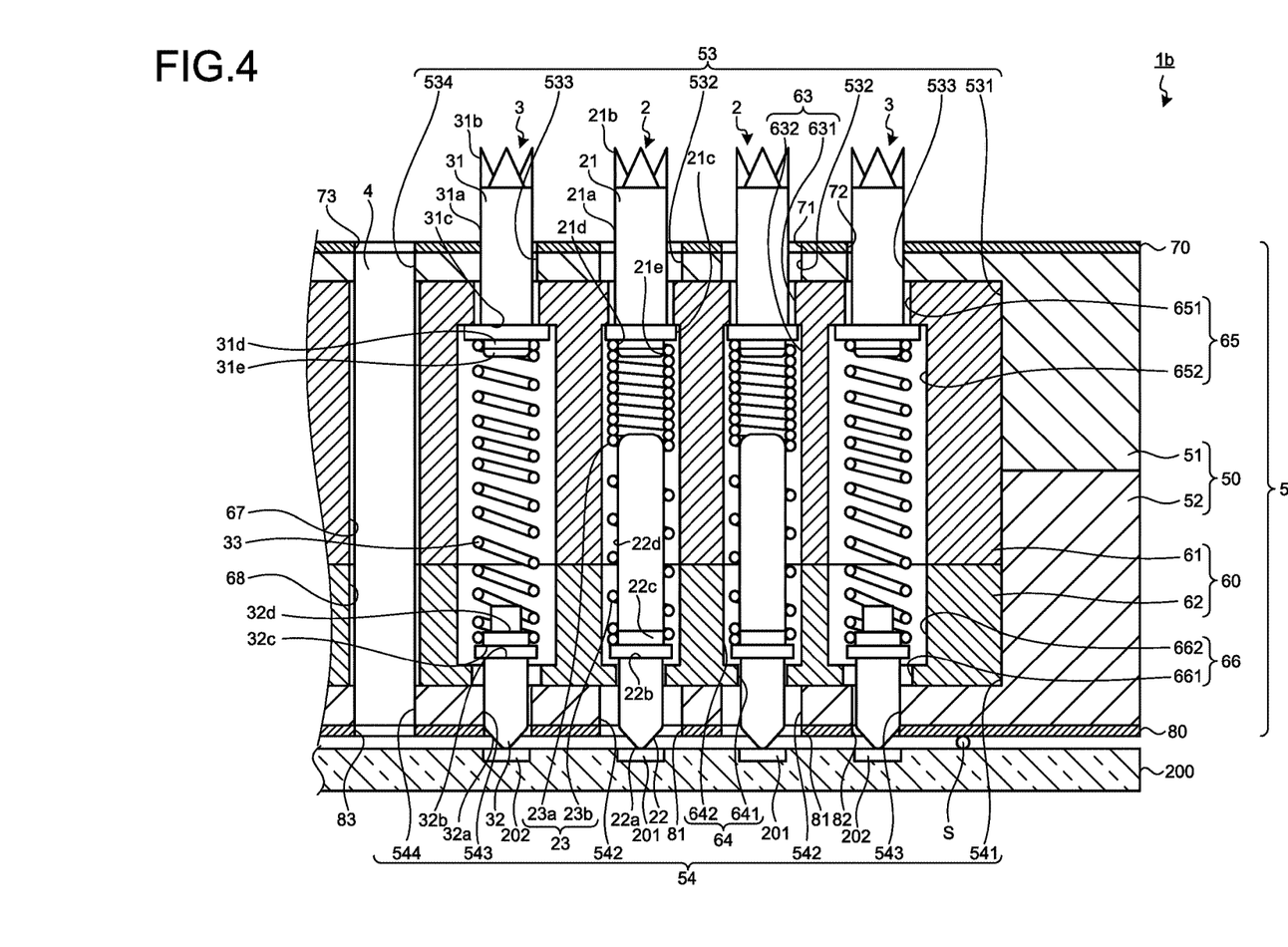
FIG. 4 is a partial sectional view illustrating a configuration of a probe unit according to a second modification of the first embodiment of the present invention.

FIG. 4 is a partial sectional view illustrating a configuration of a probe unit according to a second modification of the first embodiment. In a probe unit 1b according to the second modification, space is formed between the second insulating plate 80 and the circuit board 200.

For example, space of a predetermined interval (in the second modification, diameter of a spacer S) is formed between the second insulating plate 80 and the circuit board 200, by disposing one or a plurality of spacers S having a spherical shape. Thus, even if the probe generates heat, the heat can be radiated through the space. The spacer S may be formed in an annular shape, or the sectional surface of the spacer S may have a rectangular shape or a polygonal shape.

In the second modification described above, space is formed between the second insulating plate 80 and the circuit board 200, and the heat in the space between the second insulating plate 80 and the circuit board 200 is radiated to the outside. Consequently, it is possible to prevent the conduction characteristics of the large current probe 3 from being degraded.

Third Modification of First Embodiment

Figure 5:
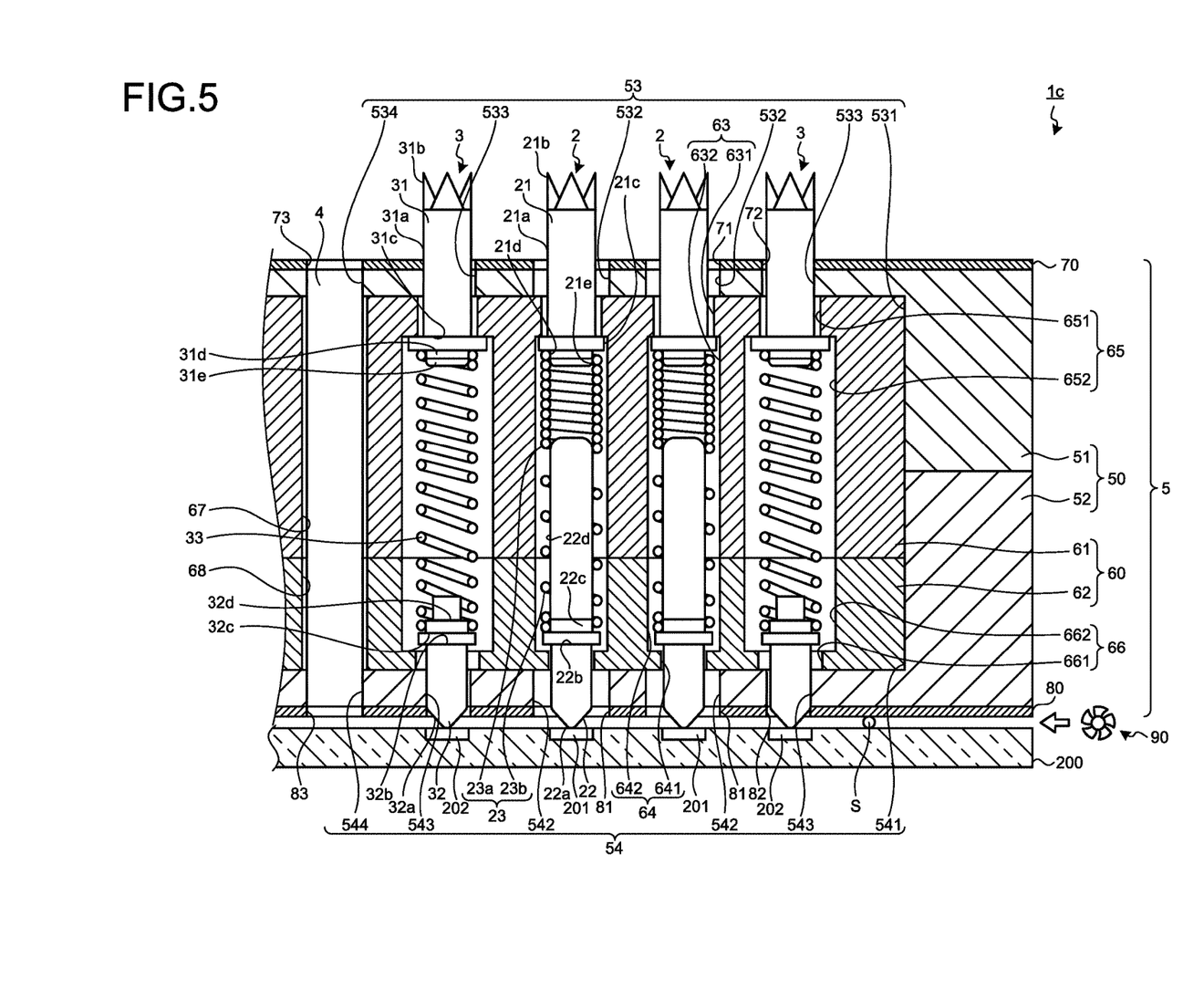
FIG. 5 is a partial sectional view illustrating a configuration of a probe unit according to a third modification of the first embodiment of the present invention.

FIG. 5 is a partial sectional view illustrating a configuration of a probe unit according to a third modification of the first embodiment. A probe unit 1c according to the third modification can further improve the heat radiation effect, by causing gas to flow through the space formed between the second insulating plate 80 and the circuit board 200 and ventilating the space, using an air supplying mechanism 90 that is implemented by a fan and the like.

Second Embodiment

Figure 6:
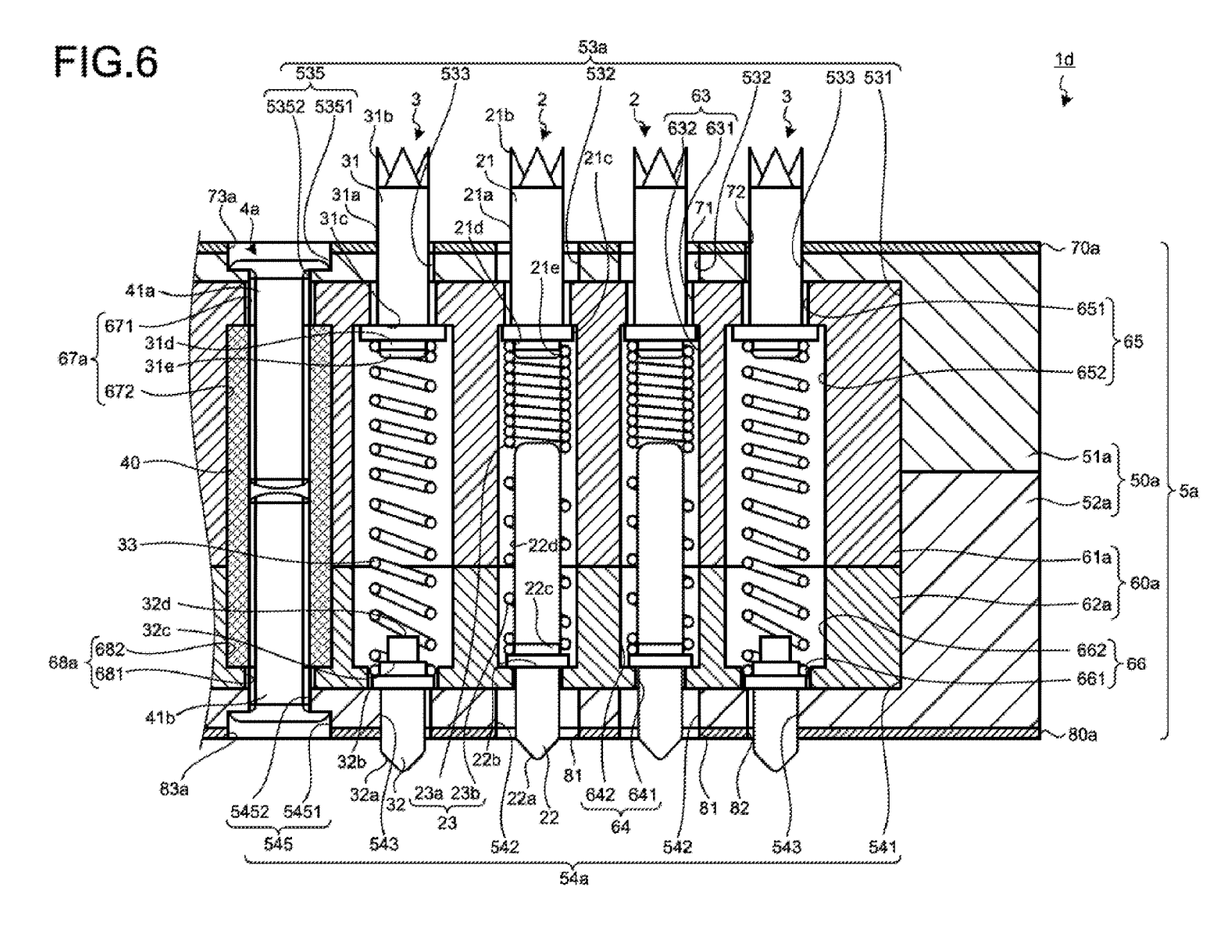
FIG. 6 is a partial sectional view illustrating a configuration of a probe unit according to a second embodiment of the present invention.

A second embodiment of the present invention will now be described. FIG. 6 is a partial sectional view illustrating a configuration of a probe unit according to the second embodiment of the present invention. The same reference numerals denote the same components as those described in FIG. 1 and the like. While in the first embodiment described above, the conductive pin 4 that is pressed into the metal block 50 is used for conduction, a metal screw and a metal nut are used for conduction in the second embodiment.

A probe unit 1d according to the second embodiment includes the signal probes 2 and the large current probes 3 described above, a conductive member 4a that can be electrically connected to each of both end portions of the large current probes 3, and a plurality of probe holders 5a that accommodate and hold the signal probes 2, the large current probes 3, and the conductive members 4a according to a predetermined pattern.

The conductive member 4a includes a metal nut 40 in a tubular shape that is formed of a conductive metal material, and two metal screws 41a and 41b that are formed of a conductive metal material and that are screwed into the metal nut 40 from respective end portions of the metal nut 40. The metal nut 40 as well as the metal screws 41a and 41b may be formed of a material such as resin, as long as the material has conductivity.

The probe holder 5a includes: a metal block 50a (conductive block) that is formed of a conductive material such as metal, and that is formed by laminating a first member 51a being placed on the upper surface side and a second member 52a being placed on the lower surface side in FIG. 6; an insulating block 60a that is formed of an insulating material such as resin, machinable ceramic, and silicon, and is accommodated inside the metal block 50a; a first insulating plate 70a that is formed of an insulating material such as resin, machinable ceramic, and silicon, that has a substantially plate shape, and that is disposed on the upper surface of the first member 51a; and a second insulating plate 80a that is formed of an insulating material such as resin, machinable ceramic, and silicon, that has a substantially plate shape, and that is disposed on the lower surface of the second member 52a.

The first member 51a and the second member 52a may be formed of a metal material including alloy such as brass, as well as any conductive material. From the viewpoint of strength as a probe holder, the first member 51a and the second member 52a are preferably formed of a metal material (including alloy).

Holder holes 53a and 54a for accommodating the signal probe 2, the large current probe 3, the conductive member 4a, and the insulating block 60a are respectively formed on the first member 51a and the second member 52a. The holder hole 53a includes the accommodation unit 531, the hole 532, and the hole 533 described above, and a hole 535 that communicates with the accommodation unit 531 and into which the conductive member 4a is inserted.

The hole 535 has a stepped-hole shape having a diameter that varies along the penetrating direction. The hole 535 includes a large diameter unit 5351 that has an opening on the upper surface side of the first member 51a, and a small diameter unit 5352 that communicates with the large diameter unit 5351 and the accommodation unit 531, and that has a diameter smaller than that of the large diameter unit 5351.

The diameter of the large diameter unit 5351 is slightly larger than that of the head part of the metal screw 41a. The diameter of the small diameter unit 5352 is smaller than that of the head part of the metal screw 41a, and substantially the same as that of the body part of the metal screw 41a.

The holder 54a includes the accommodation unit 541, the hole 542, and the hole 543 described above, and a hole 545 that communicates with the accommodation unit 541 and into which the conductive member 4a is inserted. The hole 545 has a stepped-hole shape having a diameter that varies along the penetrating direction. The hole 545 includes a large diameter unit 5451 that has an opening on the lower surface side of the second member 52a, and a small diameter unit 5452 that communicates with the large diameter unit 5451 and the accommodation unit 541, and that has a diameter smaller than that of the large diameter unit 5451. The diameter of the large diameter unit 5451 is slightly larger than that of the head part of the metal screw 41b. The diameter of the small diameter unit 5452 is smaller than that of the head part of the metal screw 41b, and substantially the same as that of the body part of the metal screw 41b.

The insulating block 60a is formed by laminating a first member 61a being placed on the upper surface side and a second member 62a being placed on the lower surface side in FIG. 6. The insulating block 60a has a substantially rectangular parallelepiped shape that can be fitted into the accommodation unit 531 and the accommodation unit 541.

The same number of the holder holes 63 and 64 as well as the holder holes 65 and 66 described above are formed on the first member 61a and the second member 62a, respectively, and formed coaxially.

In addition, the same number of holder holes 67a and 68a for accommodating the conductive member 4a are respectively formed on the first member 61a and the second member 62a, and the holder holes 67a and 68a that are insertion holes for accommodating the conductive member 4a are formed coaxially.

The holder holes 67a and 68a each have a stepped-hole shape having a diameter that varies along the penetrating direction. The holder hole 67a includes a small diameter unit 671 that has an opening on the upper surface side of the first member 61a, and a large diameter unit 672 that communicates with the small diameter unit 671 and that has a diameter larger than that of the small diameter unit 671. The diameter of the small diameter unit 671 is slightly larger than that of the body part of the metal screw 41a. The diameter of the large diameter unit 672 is substantially the same as the outer diameter of the metal nut 40.

The holder hole 68a includes a small diameter unit 681 that has an opening on the lower surface side of the second member 62a, and a large diameter unit 682 that communicates with the small diameter unit 681 and that has a diameter larger than that of the small diameter unit 681. The diameter of the small diameter unit 681 is slightly larger than that of the body part of the metal screw 41b. The diameter of the large diameter unit 682 is substantially the same as the outer diameter of the metal nut 40.

In the first insulating plate 70a, holes corresponding to the arrangement of the holes 532, 533, and 535 are provided on the upper surface of the first member 51a. More specifically, the first insulating plate 70a is provided with the holes 71 and 72 described above, and a hole 73a that is provided corresponding to the hole 535 and is capable of receiving the conductive member 4a. The diameter of the hole 73a is equal to that of the large diameter unit 5351.

In the second insulating plate 80a, holes corresponding to the arrangement of the holes 542, 543, and 545 are provided on the lower surface of the second member 52a. More specifically, the holes 81 and 82 described above, and a hole 83a that is provided corresponding to the hole 545 and is capable of receiving the conductive member 4a are formed on the second insulating plate 80a. The diameter of the hole 83a is equal to that of the large diameter unit 5451.

In the probe holder 5a, the hole 535, the hole 545, the holder hole 67a, the holder hole 68a, the hole 73a, and the hole 83a are coaxial when the insulating block 60a, the first insulating plate 70a, and the second insulating plate 80a are fixed on the metal block 50a.

In the probe holder 5a, the metal nut 40 is fitted into the hole that is formed by the holder hole 67a and the holder hole 68a. The metal screw 41a is inserted into the hole 535 and the small diameter unit 671, and the metal screw 41a is screwed into the metal nut 40. In addition, the metal screw 41b is inserted into the hole 545 and the small diameter unit 681, and the metal screw 41b is screwed into the metal nut 40.

In this process, the head part of the metal screw 41a abuts on a step part that is formed by the large diameter unit 5351 and the small diameter unit 5352. In addition, the head part of the metal screw 41b abuts on a step part that is formed by the large diameter unit 5451 and the small diameter unit 5452. Consequently, it is possible to laminate the first member 51a and the second member 52a further reliably, by screwing the metal screws 41a and 41b into the metal nut 40 to fasten the metal block 50a.

In the second embodiment described above, it is possible to obtain a probe unit suitable for allowing a large current to flow because both ends of the large current probe 3 are electrically connected to the contact target electrodes, and a large current is made to flow via the metal block 50a that comes into contact with both end portions of the large current probe 3, or the metal block 50a and the conductive member 4a that comes into contact with the metal block 50a.

In addition, in the first and the second embodiments described above, the end of each tip end portion side of each flange unit and each boundary wall surface between the large diameter unit and the small diameter unit of the holder hole may be tapered. Consequently, positioning of a direction perpendicular to the axis direction of the signal probe 2, when the signal probe 2 is fitted to the probe holders 5 and 5a can be performed more effectively.

Furthermore, in the first and the second embodiments described above, the thickness of the first insulating plate 70, 70a and that of the second insulating plate 80, 80a may be equal (same shape), or may be different.

Furthermore, in the first and the second embodiments described above, the accommodation unit that accommodates the insulating block 60, 60a is formed by laminating the first member 51, 51a, and the second member 52, 52a. However, the accommodation unit may be formed on either one of the first member 51, 51a and the second member 52, 52a.

Furthermore, in the first and the second embodiments described above, the conductive pin 4 or the conductive member 4a is used for establishing conduction. However, the configuration in which the conductive pin 4 and the conductive member 4a are not be included may be employed as long as a large current can be ensured simply with the conduction via the metal block 50, 50a.

The contact probes according to the first embodiment and the second embodiment described above are not limited to be formed by a plunger and a coil spring, but may be a pogo pin or a wire probe that obtains load by bending a wire into a bow-shape may also be used.

INDUSTRIAL APPLICABILITY

As described above, the probe unit according to the present invention is suitable for allowing a large current to flow.

REFERENCE SIGNS LIST

1, 1a, 1b, 1c, 1d probe unit
2 contact probe (signal probe)
3 contact probe (large current probe)
4 conductive pin
4a conductive member
5 probe holder
21, 31 first plunger
21a, 22a, 22f, 31a, 32a, 32f tip end portion
21b, 22e, 31b, 32e nail portion
21c, 22b, 31c, 32b flange unit
21d, 22c, 31d, 32c boss unit
21e, 22d, 31e, 32d base end portion
22, 32 second plunger
23, 33 coil spring
23a tightly wound portion
23b roughly wound portion
40 metal nut
41a, 41b metal screw
50, 50a metal block
51, 51a first member
52, 52a second member
60, 60a insulating block
70, 70a first insulating plate
80, 80a second insulating plate
100 semiconductor integrated circuit
200 circuit board

The invention claimed is:
1. A probe unit, comprising:
a first contact probe configured to contact with a first electrode of a contact target object at a first end in a longitudinal direction and contact with a second electrode of a substrate at a second end in the longitudinal direction, the first contact probe being formed of a conductive material and configured to be expandable and contractible in the longitudinal direction;
a second contact probe configured to contact with a third electrode of the contact target object at the first end and contact with the fourth electrode of the substrate at the second end, the second contact probe including:
a first contact unit formed of a conductive material and configured to contact with the third electrode;
a second contact unit formed of a conductive material and contacting with the fourth electrode; and
a coupling member configured to be expandable and contractible in the longitudinal direction and couple the first and the second contact units;
a probe holder configured to accommodate and hold the first and the second contact probes, the probe holder including
a conductive block formed of a conductive material and including a plurality of first insertion holes to which the first and the second contact probes are inserted, the conductive block contacting with each of the first and the second contact units; and
an insulating block provided inside the conductive block, the insulating block being formed of a material having an insulating property, and including a plurality of second insertion holes to which the first and the second contact probes are inserted, the insulating block at least preventing the first contact probe from loosening.

2. The probe unit according to claim 1, wherein the coupling member is formed of a material at least a surface of which has an insulating property.

3. The probe unit according to claim 1, further comprising a conductive member that is held by the probe holder, the conductive member being electrically connected to the second contact probe, and being formed of a conductive material.

4. The probe unit according to claim 3, wherein the conductive member is a conductive pin having a substantially columnar shape, and is pressed into one of the first insertion holes.

5. The probe unit according to claim 3, wherein
a first insertion hole, among the first insertion holes, into which the conductive member is inserted has a stepped shape having a diameter that increases toward outside, the conductive member includes
a conductive nut provided on the insulating block, and
two conductive screws screwed into the nut from an upper surface and a lower surface of the conductive block, and
a head portion of each of the screws abuts on a step part formed on the first insertion hole.

6. The probe unit according to claim 1, wherein the probe holder and the substrate are separated, while the first contact probe is brought into contact with the second electrode, and the second contact probe is brought into contact with the fourth electrode.

7. The probe unit according to claim 6, further comprising an air supplying mechanism configured to send gas to flow through space between the probe holder and the substrate.

8. The probe unit according to claim 1, wherein a plurality of nail portions each including a tapered tip end are provided on a tip end of at least one of the first and the second contact units, at a side that comes into contact with the third electrode or the fourth electrode.

9. The probe unit according to claim 1, wherein the probe holder further comprises:
a first insulating plate formed of an insulating material and provided on one surface of the conductive block, the first insulating plate including
first holes to which a part of the first contact probe is inserted, and
second holes to which a part of the second contact probe is inserted,
wherein the first and the second holes are positioned in correspondence with an electrode arrangement of the contact target object; and
a second insulating plate formed of an insulating material and provided on another surface of the conductive block, the second insulating plate including
third holes to which a part of the first contact probe is inserted, and
fourth holes to which a part of the second contact probe is inserted,
wherein the third and the fourth holes are positioned in a same arrangement as the first and the second holes.

* * * * *